(12) United States Patent
Ban et al.

(10) Patent No.: US 7,431,945 B2
(45) Date of Patent: Oct. 7, 2008

(54) ALLERGEN REMOVER

(75) Inventors: Takeshi Ban, Wakayama (JP); Satoshi Nagai, Wakayama (JP); Katsuyuki Takano, Wakayama (JP); Masahiro Suzuki, Wakayama (JP); Michio Yokosuka, Wakayama (JP)

(73) Assignee: Kao Corporation, Tokyo (JP)

( * ) Notice: Subject to any disclaimer, the term of this patent is extended or adjusted under 35 U.S.C. 154(b) by 296 days.

(21) Appl. No.: 10/983,733

(22) Filed: Nov. 9, 2004

(65) Prior Publication Data

US 2005/0119148 A1    Jun. 2, 2005

(30) Foreign Application Priority Data

| Dec. 2, 2003 | (JP) | ............................ 2003-402580 |
| Jul. 14, 2004 | (JP) | ............................ 2004-207472 |

(51) Int. Cl.
| A61K 33/00 | (2006.01) |
| A61K 33/04 | (2006.01) |
| A61L 9/01 | (2006.01) |
| A01N 25/00 | (2006.01) |
| A01N 59/00 | (2006.01) |
| A01N 59/02 | (2006.01) |

(52) U.S. Cl. ...................... 424/722; 424/76.8; 424/405; 424/709

(58) Field of Classification Search ................. 514/919; 424/76.8, 405, 709, 722
See application file for complete search history.

(56) References Cited

U.S. PATENT DOCUMENTS

| 4,507,219 | A |   | 3/1985 | Hughes |
| 5,916,917 | A | * | 6/1999 | Suh et al. .................... 514/544 |
| 2005/0095222 | A1 | * | 5/2005 | Suzuki et al. ............ 424/78.37 |

FOREIGN PATENT DOCUMENTS

| DE | 42 02 549 A1 | 8/1993 |
| EP | 1 394 245 A1 | 3/2004 |
| GB | 998495 | 7/1965 |
| JP | 4-37554 | 2/1992 |
| JP | 4-91197 | 3/1992 |
| JP | 7-3289 | 1/1995 |
| JP | 7-224299 | 8/1995 |
| WO | WO 98/50518 | * 11/1998 |
| WO | WO 00/73351 A1 | 12/2000 |
| WO | WO 02/100995 A1 | 12/2002 |

OTHER PUBLICATIONS

Washington state department of agriculture Mar. 21, 2006, p. 1.*
"Results of Comparative tests of detergents for carpets", National Consumer Affairs Center of Japan, Dec. 1987, pp. 1, 3-12, 15-21 and 23.
"Washing of Interior Textiles", Seni Seihin Shohi Kagaku, Science of Consumption of Textiles, vol. 23, No. 7, Jul. 25, 1982, pp. 265-270, 304.
Derwent Publications, AN 2000-342396, XP-002319795, JP 2000-063207, Feb. 29, 2000.

* cited by examiner

*Primary Examiner*—Johann Richter
*Assistant Examiner*—Ernst Arnold
(74) *Attorney, Agent, or Firm*—Oblon, Spivak, McClelland, Maier & Neustadt, P.C.

(57) ABSTRACT

The invention relates to an allergen remover composition containing component (a): an organic compound forming an azeotropic mixture with water and having an azeotropic point of lower than 100° C. with water at 1013.25 hPa, component (b): a component which upon evaporation of a liquid component in the allergen remover, forms a solid containing a compound represented by the following general formula (1) or component (b'): a combination of potassium ion, sodium ion and sulfate ion at a potassium ion/sodium ion molar ratio of from 2/8 to 9/1 and component (c): water.

$$K_xNa_y(SO_4)_2 \qquad (1)$$

wherein x is a number of 0.8 to 3.6, y is a number of 0.4 to 3.2, and x+y is 4.

17 Claims, No Drawings

ALLERGEN REMOVER

FIELD OF THE INVENTION

The present invention relates to an allergen remover.

BACKGROUND OF THE INVENTION

Dust formed from dead bodies of mites, chironomids and cockroaches or their excrements, broken materials of pet hair, pollen, and spores of mold are considered to act as antigen (allergen) to cause allergy symptoms, and the influence of the allergen on the human body is a social problem. As the environment in a room is made comfortable, propagation of mites is facilitated, and the presence of substances causing allergic diseases such as asthma, atopic dermatitis and allergic rhinitis is actualized. In particular, mites such as *Dermatophagoides pteronyssinus, Tyrophagus putrescentidae* or *Dermatophagoides farinae* live and grow in matting such as tatami mat and carpet and bedding such as blanket and futon, and control of such mites is a matter of high concern not only for those who have allergic diseases but also in general homes.

The present inventors developed a method of efficiently removing allergen in usual cleaning and an allergen remover used in the method, and disclosed them in WO-A 02/100995. According to this method, allergen can be easily and efficiently removed in daily cleaning by simultaneously using a cleaning instrument such as a vacuum-cleaner.

As disclosed in results of comparative tests of detergents for carpets (National Consumer Affairs Center of Japan, December 1987) and "Washing of Interior Textiles" pp. 265-270 in "Seni Seihin Shohi Kagaku" (Science of Consumption of Textiles), Vol. 23, No. 7, published in Jul. 25, 1982), a carpet cleaner for removing soil smudge adhering to carpets etc. and a carpet cleaner for removing stains with juice and coffee are known.

SUMMARY OF THE INVENTION

The present invention relates to an allergen remover composition containing the following components (a), (b) or (b') and (c):

Component (a): an organic compound forming an azeotropic mixture with water and having an azeotropic point of lower than 100° C. with water at 1013.25 hPa, Component (b): a component which upon evaporation of a liquid component in the allergen remover, forms a solid containing a compound represented by the following general formula (1)

$$K_xNa_y(SO_4)_2 \quad (1)$$

wherein x is a number of 0.8 to 3.6, y is a number of 0.4 to 3.2, and x+y is 4,

Component (b'): a combination of potassium ion, sodium ion and sulfate ion at a potassium ion/sodium ion molar ratio of from 2/8 to 9/1, Component (c): water.

That is, the present invention relates to an allergen remover composition containing components (a), (b) and (c). Alternatively the present invention relates to an allergen remover composition containing components (a), (b') and (c).

The present invention also relates to a method of removing allergen, which including cleaning it with the above shown allergen remover composition. In addition, the present invention relates to use of the above shown composition as as an allergen remover.

DETAILED DESCRIPTION OF THE INVENTION

The solid component in the invention in WO 02/100995 is preferably a sulfate in respect of safety and easy removal by a vacuum-cleaner etc., and particularly alkali metal or alkaline earth metal sulfates are solid components excellent in an effect of removing allergen.

However, these components are poor insolubility in water, and particularly the solubility of sodium sulfate in water is significantly reduced at a temperature of 5° C. or less, and thus when the composition is stored at low temperatures (particularly stored at 5° C. or less), sulfate crystals are formed, and the crystals grow largely and are hardly re-dissolved even after returning to room temperature. Accordingly, if the concentration of the sulfate is to be increased to further increase the effect of removing allergen, the sulfate cannot be blended in an amount exceeding the solubility thereof at low temperatures.

The carpet cleaner disclosed in the results of comparative tests of detergents for carpets (National Consumer Affairs Center of Japan, December 1987) and "Washing of Interior Textiles" on pp. 265-270 in "Seni Seihin Shohi Kagaku" (Science of Consumption of Textiles), Vol. 23, No. 7, published in Jul. 25, 1982) is used for removing smudge but not for positively removing allergen, and thus blushing for removing smudge or its related operation is essential, and an operation of foaming to raise smudge is also important. Further, an increase in frequency of the treatment causes deterioration in carpets, and the frequency of the treatment should be limited to about 2 to 3 per month so that there is no substantial effect of removing allergen.

The present invention provides an allergen remover, a method of removing allergen with the allergen remover and use of the allergen remover, wherein the effect of removing allergen can be enhanced by improving the low-temperature stability of the allergen remover containing a sulfate to further increase the content of the sulfate.

The present invention relates to an agent for effectively removing allergen hardly removable by usual cleaning, and in particular to an agent for efficiently removing allergen that is a substance acting as an antigen of allergen, such as dead bodies or excrement of mites, spores of mold, pollen etc.

The allergen remover of the present invention can enhance its effect of removing allergen because the low-temperature stability of the allergen remover containing a sulfate has been improved thus allowing the amount of the sulfate to be increased.

<Component (a)>

The component (a) in the present invention is an organic compound forming an azeotropic mixture with water and having an azeotropic point of lower than 100° C. with water at 1013.25 hPa (760 mmHg), and among compounds forming azeotropic mixtures with water described in Table 8-43 on page II-147 in "Kagaku Binran Kisohen" (Handbook of Chemistry, Fundamental Version), 4th edition, edited by the Chemical Society of Japan and published by Maruzen Co., Ltd., a compound having an azeotropic point of lower than 100° C., preferably 60 to 90° C., can be used. By incorporating the component (a), drying of a material treated with the allergen remover of the present invention is promoted, and formation of an allergen-containing solid by the action of component (b) or (b') is promoted.

Preferable examples of the component (a) include ethanol, cyclohexane, cyclohexanol, cyclohexanone, cyclohexane, toluene, 1-butanol, 2-butanol, 1-propanol, 2-propanol, 1-hexanol, hexane, 1-heptanol, 1-pentanol, 2-pentanol etc., and C2 to C7 alcohol compounds are preferable. In particular, ethanol, 1-propanol and 2-propanol are preferable in respect of the effect of removing allergen.

<Components (b) and (b')>

The component (b) in the present invention is the one which upon evaporation of a liquid component in the allergen remover, forms a solid containing a compound represented by the following general formula (1), and the compound consists of a combination of potassium ion, sodium ion and sulfate ion.

$$K_x Na_y (SO_4)_2 \qquad (1)$$

wherein x is a number of 0.8 to 3.6, preferably 1.2 to 3.2, more preferably 1.6 to 2.8, y is a number of 0.4 to 3.2, preferably 0.8 to 2.8, more preferably 1.2 to 2.4, and x+y is 4.

To confirm formation of the compound of the general formula (1) upon evaporation of the liquid component in the allergen remover, known methods such as powder X-ray diffraction method, electron beam diffraction method etc. can be used.

A diffraction pattern of the compound of the general formula (1) can be identified by using JCPDS: 20-926, 20-927, 20-928. A sample used in analysis is prepared by the following method.

<Preparation of the Sample>

A trigger container used in Smoother (trade name) commercially available from as an ironing finisher by Kao Corporation was charged with the allergen remover, and used to spray 1 g remover, from a height of 30 cm, onto a glass plate 50 by 50 centimeters square under the environment of 23° C./50% RH, followed by drying at 23° C. in 50% RH for 1 hour. This operation was conducted 10 times, and the resulting precipitate was collected and milled in a glass mortar to give the sample. When Smoother was not available, a trigger sprayer described later can be used.

The component (b') in the present invention is a combination of potassium ion, sodium ion and sulfate ion at a potassium ion/sodium ion molar ratio of from 2/8 to 9/1, preferably 3/7 to 8/2, more preferably 4/6 to 7/3. The (potassium ion+sodium ion)/sulfate ion molar ratio is preferably 1/1 to 4/1, more preferably 1.5/1 to 3/1, still more preferably 1.8/1 to 2.2/1.

The concentration of potassium ion and sodium ion in the allergen remover can be quantified directly by an atomic absorption method, and the concentration of sulfate ion in the allergen remover can be measured by ion chromatography.

The component (b) can be obtained by:

(I) a method of mixing an alkaline substance selected from potassium hydroxide, sodium hydroxide, potassium carbonate, sodium carbonate, potassium bicarbonate and sodium bicarbonate and an acidic substance selected from sulfuric acid, sodium hydrogen sulfate and potassium hydrogen sulfate so as to be in accordance with the a/b molar ratio in the general formula (1), or (II) a method of mixing sodium sulfate and potassium sulfate so as to be in accordance with the a/b molar ratio in the general formula (1).

The component (b') can be obtained by:

(I) a method of mixing an alkaline substance selected from potassium hydroxide, sodium hydroxide, potassium carbonate, sodium carbonate, potassium bicarbonate and sodium bicarbonate and an acidic substance selected from sulfuric acid, sodium hydrogen sulfate and potassium hydrogen sulfate so as to be in accordance with the indicated molar ratio, or (II) a method of mixing potassium sulfate and sodium sulfate so as to be in accordance with the indicated molar ratio.

For both the components (b) and (b'), the method (I) causes heat generation and possible deterioration of other components due to use of a very strong base or acid, and requires attention for safety in handling, and thus the method (II) is preferably used.

When the components (b) and (b') are obtained by using the method (II), potassium sulfate/sodium sulfate are mixed in a molar ratio of 2/8 to 9/1, preferably 3/7 to 8/2, more preferably 4/6 to 7/3.

<Component (c)>

The component (c) in the present invention is water which is the balance (by which the whole volume is adjusted to 100 mass %) of the remover containing the component (a), component (b) or component (b'), and other components, and also acts a solvent for a part of the component (b) or (b'). Water used may contain a certain amount of metallic ion (the ion may be the same as component (b) or (b')), but deionized water is used preferably in respect of shelf stability.

<Component (d)>

For the purpose of further improving the effect of removing allergen in the present invention, a repellent (component (d)) for arthropods such as mites as an allergen source is preferably contained. The arthropod repellent in the present invention is defined as a compound having a repellent effect on *Dermatophagoides farinae*, and is a compound or a mixture by which the degree of repellency of *Dermatophagoides farinae* is 50% or more as a result of examination by the following entry inhibition method.

Method of Measuring the Degree of Repellency (Entry Inhibition Method)

Test medium: A 9 cm diameter Petri dish is fixed to an adhesive sheet plate, and a Petri dish of 4 cm in diameter is then placed in the center of the 9 cm dish, concentrically. A paper filter, which is impregnated with 0.5 ml of 10 mass % test compound in ethanol, dried for 1 hour under 25 degree centigrade—60% relative humidity, and cut in a 4 cm circle, is placed in bottom of the 4 cm dish. Then, 500 mg feed consisting of a powder feed for mouse mixed with dry yeast is placed in the center of the filter paper. And about 10,000 mites (*Dermatophagoides farinae*) together with a medium are placed between the 4 cm and 9 cm dishes.

Reference medium: A reference medium is prepared in the same manner as above except that another 9-cm Petri dish is fixed to the same adhesive sheet plate, and in the test medium, only ethanol is used as the solution with which the filter paper is impregnated.

These Petri dishes are placed under the condition of 25° C./75% RH, and 48 hours later, the number of mites having entered the feed in the center is counted, and from a difference in count between the test medium and reference medium, the degree of repellency is calculated according to the following equation. The count of mites is measured under a stereoscopic microscope.

Degree of repellency=(1−number of entering mites in the test medium/number of entering mites in the reference medium)× 100

A compound preferable in respect of safety as the component (d) in the present invention is an extract obtained from a natural material, a compound obtained by isolating, from a natural material, a compound occurring in an extract of the natural material, or a compound obtained by synthesizing a compound occurring in an extract of a natural material, and a mixture thereof, and specifically the following compounds are preferable.

(d-1): a synthetic or isolated perfume selected from jasmone, dihydrojasmone, methyl jasmonate, methyl dihydrojasmonate, methyl eugenol, isoeugenol, amyl salicylate, isoamyl salicylate, hexyl salicylate, cis-3-hexenyl salicylate, benzyl salicylate, L-menthone, L-carvone, benzaldehyde, benzyl alcohol, 2-phenyl ethyl alcohol, 2-phenoxy ethanol, α-amylcinnamic aldehyde, cinnamyl alcohol, cinnamic aldehyde, ethyl cinnamate, propyl cinnamate, isopropyl cinnamate, cinnamyl acetate, amyl benzoate, isoamyl benzoate, hexyl benzoate, cis-3-hexenyl benzoate, heptyl benzoate, octyl benzoate, farnesol, nerolidol, phetol, tetrahydrolinalool, bornyl acetate, myrcenyl acetate, cedryl acetate, lavandulyl acetate, citronellyl isobutyrate, terpinyl propionate, linalyl formate, citronellyl tigrate, nopyl acetate, vetiveryl acetate, lyral, citronellyloxyacetaldehyde, 2,6,10-trimethyl-9-undecanal, α-ionone, β-ionone, irone, α-damascone, β-damascone, nootkatone, cedryl methyl ether, isomenthone, citronellal, linalool, citronellol, citral, p-menthane, α-pinene, β-pinene, d-limonene, geraniol, α-terpineol, β-terpineol, γ-terpineol, 1,8-cineol, p-menthan-8-ene-1,2-diol, eugenol, benzyl formate, benzyl acetate, benzyl propionate, benzyl butyrate, benzyl valerate, benzyl caproate, linalool and α-hexyl succinic aldehyde, or a mixture thereof;

(d-2): a vegetable essential oil selected from lemon grass oil, lavender oil, orange oil, vetiver oil, patchouli oil, cananga oil, clove oil, cajeput oil, citronella oil, natsumegu oil, pepper oil, sandal wood oil, bulk oil, cagin oil, ginger oil, campo oil, cuvevie oil, cone mint oil, anise oil, lang oil, cinnamon oil, mease oil, palomalosa oil, fennel oil, calamus oil, taimes oil, neam oil and cinnamon leaf oil;

(d-3): hinokitiol and/or a hinokitiol derivative;

(d-4): a plant extract extracted with alcohol from persimmon leaves, Japanese fatsia, mugwort, celery and dokudami.

In the present invention, the compounds (d-1) and (d-2) are particularly preferable, and the compound (d-1) is particularly preferably jasmone, dihydrojasmone, methyl jasmonate or methyl dihydrojasmonate, and the vegetable essential oil (d-2) is particularly preferably lavender oil, clove oil, cinnamon oil or lemon grass oil.

<Component (e)>

In the present invention, a water-soluble polymer compound can be contained as component (e). The water-soluble compound in the present invention is defined as a compound showing a uniform outward appearance upon being dissolved in an amount of 0.5 g in 100 g water at 20° C., pH 7. Specific examples include a water-soluble polymer selected from:

(i) a cellulose derivative and/or processed starch, (ii) a homopolymer of acrylic acid or methacrylic acid and/or a copolymer of acrylic acid or methacrylic acid and at least one vinyl monomer, as well as a salt thereof, (iii) a copolymer obtained by polymerizing acrylic acid and/or methacrylic acid with at least one alkyl ester thereof or a salt thereof, and (iv) a polymer obtained by polymerizing a monomer having a cationic group and vinyl group or allyl group in the molecule.

Particularly, the cellulose derivative and/or processed starch (i) is more excellent in respect of the effect of removing allergen.

The cellulose derivative (i) is preferably at least one member selected from hydroxy alkyl (C1 to C3) cellulose, alkyl (C1 to C3) cellulose (preferably methyl cellulose, ethyl cellulose), carboxymethyl cellulose, and cationic cellulose having a quaternary ammonium group.

The processed starch (i) includes hydroxy alkyl (C1 to C3) starch, alkyl (C1 to C3) starch, carboxymethyl starch, cationic starch having a quaternary ammonium group, and processed starch produced by reducing the viscosity of the above starch by an oxidizing agent such as hydrogen peroxide or sodium hypochlorite or an enzyme.

Particularly preferable in the present invention is a polymer compound wherein a part or all of hydrogen atoms in hydroxyl groups in cellulose, a cellulose derivative selected from hydroxy alkyl (C1 to C3) cellulose and alkyl (C1 to C3) cellulose, starch, and a starch derivative selected from hydroxy alkyl (C1 to C3) starch, alkyl (C1 to C3) starch and carboxymethyl starch were replaced by groups represented by the following general formula (2).

$$-R^5-(OR^6)_e-E-R^7 \qquad (2)$$

Meaning of each symbol in the formula is as follows:

$R^5$ is a C1 to C6 alkylene group which may be substituted with a hydroxy or oxo group, and is preferably an ethylene group, propylene group, trimethylene group, 2-hydroxytrimethylene group, 1-hydroxytrimethylene group, 1-oxoethylene group, 1-oxotrimethylene group or 1-methyl-2-oxoethylene group, particularly preferably a 2-hydroxytrimethylene group or 1-hydroxytrimethylene group;

$R^6$ is a C1 to C6 alkylene group, preferably an ethylene group or propylene group;

$R^7$ is a C4 to C30 hydrocarbon group or a C1 to C5 sulfoalkyl group, which may be substituted by a hydroxy group. A straight or branched alkyl or alkenyl group or a C4 to C30 hydrocarbon group such as a steroid structure-containing hydrocarbon group, preferably cholesteryl group, is preferably specified. More preferable is a C5 to C25, even more preferably C6 to C20, alkyl group which may be substituted with a hydroxy group. Even more preferable is a 2-sulfoethyl group, 3-sulfopropyl group, 3-sulfo-2-hydroxypropyl group or 2-sulfo-1-(hydroxymethyl)ethyl group.

E is an ether group or oxycarbonyl group, preferably an ether group;

e is the average number of moles added, which is a number of preferably 0 to 50, more preferably 0 to 40, still more preferably 0 to 30, further more preferably 0 to 20, further more preferably 10 to 20. $(OR^6)$s whose number is e may be the same or different.

The degree of substitution of the alkyl or hydroxyalkyl group in the cellulose derivative and starch derivative is preferably 0.01 to 3.5, more preferably 0.1 to 3, still more preferably 1 to 3, further more preferably 1.5 to 2.8, per constituent monosaccharide residue.

The degree of substitution of the substituent group in the general formula (2) is preferably 0.0001 to 1, more preferably 0.0005 to 0.5, still more preferably 0.001 to 0.1, further more preferably 0.001 to 0.05, per constituent monosaccharide residue.

When $R^7$ is a sulfoalkyl group in the general formula (2), the degree of substitution of the sulfoalkyl group is preferably 0 to 1, more preferably 0 to 0.8, still more preferably 0 to 0.5, per constituent monosaccharide residue.

The weight-average molecular weight of the cellulose derivative (i) is preferably 10,000 to 2,000,000, more preferably 50,000 to 1,500,000, still more preferably 100,000 to 600,000. The weight-average molecular weight can be determined by high performance anion exchange chromatography (HPAEC) equipped with a pulse amperometric detector or by capillary electrophoresis.

The cellulose derivative (i) can be obtained by a method described in WO-A 00/73351, by reacting a cellulose derivative or a starch derivative with a compound represented by $R^8$—$(OR^6)_e$-E-$R^7$, in which $R^8$ is a C3 to C6 epoxylated alkyl group or a C1 to C6 halogenated alkyl group which may be substituted with a hydroxy group, or a carboxyl group or a C2 to C6 carboxy alkyl group or a derivative thereof, and $R^6$, e, E and $R^7$ each have the same meaning as defined above, and, optionally sulfonating the product with a usual sulfonating agent.

The water-soluble polymer compound (ii) is a homopolymer of acrylic acid or methacrylic acid and/or a copolymer of acrylic acid or methacrylic acid and at least one vinyl monomer as well as a salt thereof. In the case of the copolymer, the monomer unit derived from acrylic acid or methacrylic acid is desirably 30 mol % or more, preferably 50 mol % or more.

The weight-average molecular weight is preferably 1,000 to 6,000,000, more preferably 5,000 to 1,000,000, still more preferably 10,000 to 500,000. The weight-average molecular weight can be determined by gel permeation chromatography with polyethylene glycol as standard.

The water-soluble polymer compound (iii) is a copolymer obtained by polymerizing acrylic acid and/or methacrylic acid with at least one alkyl ester thereof, or a salt thereof, and the number of carbon atoms in the alkyl group in the alkyl ester is 8 to 20, preferably 10 to 18. The molecular weight of (iii) is 100 to 1,000,000, preferably 500 to 500,000, more preferably 1,000 to 100,000.

The water-soluble polymer compound (iv) is preferably a polymer produced by polymerizing acryloyl (or methacryloyl) aminoalkyl (C1 to C5)-N,N,N-trialkyl (C1 to C3) quaternary ammonium salt, acryloyl (or methacryloyl) oxyalkyl (C1 to C5)-N,N,N-trialkyl (C1 to C3) quaternary ammonium salt, N-(ω-alkenyl (C3 to C10)-N,N, N-trialkyl (C1 to C3) quaternary ammonium salt or N,N-di(ω-alkenyl (C3 to C10))-N,N-dialkyl (C1 to C3) quaternary ammonium salt, or a copolymer copolymerizable therewith.

When the water-soluble polymer compound (iv) is a copolymer, the monomer unit derived from the compound having the above cation group and vinyl group is preferably 50 to 100 mol %, more preferably 70 to 100 mol %, still more preferably 90 to 100 mol %. The weight-average molecular weight is preferably 1,000 to 5,000,000, more preferably 5,000 to 2,000,000, still more preferably 100,000 to 1,000,000.

<Component (f)>

For the purpose of improvement of the shelf stability of the liquid composition and regulation of the viscosity thereof, a hydrotrop and a viscosity adjuster may be contained as component (f) in the present invention to such an extent that the effect of the present invention is not hindered.

As the hydrotrop, benzene sulfonic acid substituted with one to three C1 to C3 alkyl groups or a salt thereof can be used. As the viscosity regulator, partially crosslinked polyacrylic acid, hydroxyethyl cellulose, carboxymethyl cellulose, xanthane gum etc. can be compounded as thickener. Polyethylene glycol (molecular weight=300 to 4000), polypropylene glycol (molecular weight=300 to 2000), glycerin, polyglycerin (degree of condensation, 2 to 10), sorbitol, pentaerythritol etc. can be compounded as thinner.

<Other Components>

Other components include water-soluble organic solvents other than component (a), for example, an acid or alkali as a pH adjusting agent described later, methanol, a glycol solvent described in JP-A 4-91197, a phenyl ether solvent described in JP-A 7-224299, and a glyceryl ether solvent described in JP-A 7-3289, colorants for coloring the allergen remover, polymers covering allergen thereby inhibiting its expression, allergen denaturants denaturing allergen, bactericidal/acaricidal agents, antibacterial/antifungal agents for inhibiting generation of bacteria and fungi in the allergen remover, and a propellant for incorporation of the remover as aerosol. The amount of materials which may suppress formation of a solid from component (b) or (b') is sufficiently examined, and materials estimated to exhibit an allergen symptom should not be compounded.

In adjusting pH, an alkali metal hydroxide, sulfuric acid etc. may be contained, and their ion is included as component (b) or (b'). In the present invention, organic compounds other than the component (a), component (d), component (e), methanol and an organic propellant for aerosol are referred to as component (g).

In the present invention, the compound precipitated by drying may contain other components other than an inorganic solid derived from component (b) or (b'), but is preferably composed mainly of component (b) or (b') in consideration of releasability from the surface of an object.

<Allergen Remover>

The allergen remover of the present invention is in the form of an aqueous solution wherein the component (b) or (b') and if necessary the component (d), component (e) and an arbitrary component are dissolved in component (a) and water as component (c) and if necessary a solvent.

Particularly, component (b) or (b') is important in the present invention, and as drying proceeds, component (b) or (b') is precipitated as an inorganic salt to function in collecting and releasing an allergen substance from the surface of an object. Specifically, when an object is sprayed with or dipped in the allergen remover of the present invention and then dried, an inorganic salt formed from component (b) or (b') with a cation and anion as counterion is precipitated on the surface of the object. This inorganic salt is precipitated while incorporating living things such as mites and allergen such as their dead bodies or excrements. This salt is removed by wiping away with a cloth such as a towel or with a cleaning instrument such as a vacuum-cleaner, whereby the allergen can be easily removed.

The component (b) or (b') is contained such that the total of potassium ion, sodium ion and sulfate ion becomes 0.005 mass % or more, preferably 0.01 mass % or more, still more preferably 0.1 mass % or more, in order to exhibit the effect of removing allergen. The component (b) or (b') can be compounded in a content of up to 10 mass % in consideration of its influence on the feeling in touch of a treated surface, but the content is preferably 5 mass % or less, more preferably 3 mass % or less, in order to prevent the solid derived from component (b) or (b') from remaining on the surface of an object.

The concentration of potassium ion and sodium ion in the allergen remover can be quantified directly by an atomic absorption method, and the concentration of sulfate ion in the allergen remover can be measured by ion chromatography.

The component (a) in the present invention is used to promote the functions of component (b) or (b'). That is, the component (a) is used for the purpose of promotion of drying after spraying or coating and promotion of precipitation of an inorganic salt derived from component (b) or (b') on the surface of an object. To achieve such effects in the present invention, the content of component (a) in the allergen remover is preferably 1 to 70 mass %, more preferably 5 to 60 mass %, still more preferably 15 to 60 mass %.

For the purpose of improving the effect of removing allergen in the present invention, the components (d) and (e) are preferably contained in the allergen remover.

The content of component (d) is preferably 0.001 to 2 mass %, more preferably 0.005 to 1 mass %, still more preferably 0.01 to 0.5 mass %. When a perfume component is compounded besides the component (d), the total of the perfume component and component (d) is preferably 2 mass % or less, more preferably 1 mass % or less, still more preferably 0.5 mass % or less.

The content of component (e) is preferably 0.005 to 10 mass %, more preferably 0.01 to 5 mass %, still more preferably 0.05 to 1 mass %.

In the present invention, the component (f) can be contained for improvement of shelf stability and regulation of viscosity, but because it is important that the effect of the invention is not hindered, the content of component (f) in the allergen remover is lower than 1 mass %, preferably lower than 0.5 mass %, more preferably lower 0.2 mass %.

In the present invention, the content of water as component (c) in the allergen remover is preferably 30 to 99 mass %, more preferably 30 to 95 mass %, still more preferably 40 to 85 mass %.

The pH of the allergen remover of the present invention at 20° C. is adjusted to 3 to 9, preferably 4 to 8. As a pH adjusting agent, a combination of component (b) or (b'), that is, sulfuric acid, sodium hydroxide, potassium hydroxide, sodium carbonate and potassium carbonate is preferably used.

The allergen remover of the present invention is desirably composed of component (a), component (b) or (b'), component (c) and if necessary component (d) and component (e) in a total amount of preferably 95 to 100 mass %, more preferably 98 to 100 mass %, and is more desirably composed substantially of components (a) to (e) only or components (a), (b'), (c), (d) and (e) only.

For the purpose of easiness in treatment of an object and improvement in the effect of removing allergen, the viscosity of the allergen remover of the present invention at 20° C. is adjusted to 15 mPa·s or less, preferably 1 to 10 mPa·s. By adjustment to such viscosity, an object can be treated uniformly, and it is possible to promote drying or precipitation of component (b) or (b').

The viscosity mentioned in the present invention is measured in the following manner. First, Rotor No. 1 is fit into a Brookfield viscometer model BM manufactured by TOKIMEC INC. A tall beaker is charged with a sample and regulated at 20° C. in a thermostatic chamber at 20° C. The sample regulated in the thermostatic bath. The number of revolutions of the rotor is set at 60 rpm, and the viscosity of the sample 60 seconds after rotation is initiated is determined as the viscosity in the present invention.

<Method of Removing Allergen>

The method of removing allergen by using the allergen remover of the present invention is described.

First, an object of treatment such as a carpet, tatami mat, futon etc. is sprayed by a sprayer with a suitable amount of the allergen remover, then left and dried. During this drying, the components (a) and (c) are volatilized, and there remains a solid incorporating allergen, consisting of an inorganic salt composed of component (b) or (b'). In this solid, a plurality of small solids incorporating allergen have adhered during drying to one another thus forming a large solid (when the solid is expressed as sphere, its diameter upon use in a household carpet is about 0.03 to 0.1 mm depending on the condition where it is used).

Then, the large solid is removed by a cleaning instrument such as a vacuum-cleaner thereby removing the allergen. The allergen has been incorporated into the inorganic salt composed of component (b) or (b'), and the solid is large so that even when suctioned with a vacuum-cleaner, the solid can be easily suctioned highly safely without scattering the allergen.

As the sprayer, a trigger sprayer or an aerosol sprayer is preferably used, and particularly the trigger sprayer is more preferable.

When the trigger sprayer is used, the sprayer is preferably the one jetting the remover in an amount of 0.1 to 2.0 g, preferably 0.2 to 1.5 g, more preferably 0.3 to 1.0 g, by one stroke. As the container in the trigger sprayer used in the present invention, a pressure-accumulating trigger disclosed in JP-A(U) 4-37554 is particularly excellent in respect of the uniformity of spray.

When the aerosol sprayer is used, the sprayer is preferably the one jetting the remover in an amount of 0.5 to 5.0 g, preferably 1.0 to 3.0 g, per second. The propellant usable in the aerosol sprayer includes a liquefied propane gas, dimethyl ether, nitrogen, carbon dioxide, air etc. Among them, the liquefied propane gas is preferable in respect of jetting properties, and nitrogen, carbon dioxide and air are preferable in respect of safety.

With respect to jetting properties, the trigger sprayer is preferably the one which sprays a liquid on an area of 100 to 800 $cm^2$, preferably 150 to 600 $cm^2$ when an object placed vertically on the ground is sprayed with the liquid from a place apart by 15 cm. In the present invention, the component (b) or (b') is sprayed in an amount of 1 to 10 mg, preferably 1 to 5 mg, per 1000 $cm^2$ of an object and then dried to give a high effect of removing allergen.

The sprayer is preferably the one hardly foaming a liquid. The preferable sprayer in the present invention is the one which gives foam with a height of 5 cm or less, preferably 3 cm or less, still more preferably 1 cm or less, upon spraying 10 g test solution into a 100 ml colorimetric tube (made of hard glass, common fitting, body diameter 28 mm×length 260 mm, taper 24/30, available from As One Co., Ltd.) under the condition of 23° C.

As drying, natural drying is easy, but sufficient drying is promoted preferably by ventilation or with an electric fan or a ventilator. Force-drying with hot air or hot wind is also usable. When the surface of an object is wetted, it is important that the surface of the object is not rubbed with a brush etc. or not suctioned with a vacuum-cleaner, or feet are not set on the surface. When the surface of the object is rubbed with a brush etc., a solid incorporating allergen, consisting of an inorganic salt composed of component (b) or (b'), is hardly formed thus reducing the effect of removing allergen.

The object to which the allergen remover of the present invention is applied includes a carpet, tatami mat, cloth sofa, rug, flooring, other hard surfaces in a house from which allergen is desired to be removed, bedding such as futon, pillow and bed pad, stuffed toy, cloth cushion etc. The allergen remover of the present invention is preferable because, after application, feeling in touch of textiles, particularly raised textiles such as a carpet, can be improved by removing the allergen remover, e.g. by suction with a vacuum-cleaner, with an applied suitable frictional force.

EXAMPLES

Next, examples according to the present invention will be explained. These examples are intended to describe preferred embodiments of the present invention but are not intended to be limiting of the invention.

The allergen removers shown in Table 1 were prepared, and their effect of removing allergen and low-temperature stability were evaluated. The evaluation results are shown in Table 1.

(1) Evaluation of the Effect of Removing Allergen

A used carpet (Sanseceal CL-1, a carpet manufactured by Sangetsu Co., Ltd.) used for 3 years in a home was cut into a piece 10 by 10 centimeters square.

The cut carpet was sprayed uniformly with 0.3 g sample [A trigger container in Smoother (Kao Corporation) commercially available as an ironing finisher was used. The amount of spray by one stroke was 0.3 g, and when the surface of an object placed vertically on the ground was sprayed with a liquid from a place apart by 15 cm, the area sprayed with the liquid was 420 cm$^2$], and the sample was dried at room temperature for 30 minutes, and then suctioned for 1 second with a vacuum-cleaner with a suctioning power of 250 W (CV-CD4, Hitachi, Ltd) equipped with a new paper bag. This operation was repeated 20 times. It was confirmed that given the allergen removers in Examples 2, 3 and 4 in Table 1, the feeling of the carpet after suction with the vacuum-cleaner was improved and the touch was improved.

Thereafter, 50 ml of a phosphate buffer solution, pH 7.4±0.1 (that is, a solution of 0.144 g/L $KH_2PO_4$, 9.00 g/L NaCl and 0.795 g/L $Na_2HPO_4.7H_2O$ in water, referred to hereinafter as PBS) was used to extract allergen collected in the paper bag (the resulting extract is called the "extract of removed allergen"). The allergen remaining on the carpet was extracted with 50 ml PBS (the resulting extract is called the "extract of remaining allergen").

The concentration of Der f II (allergen contained in *Dermatophagoides farinae*) in each extract was quantified by sandwich ELISA. Sandwich ELISA was conducted in the following manner.

1. Monoclonal antibody 15E11 (Seikagaku Corporation) is diluted with PBS to have a concentration of 2 μg/ml, pipetted into a well (50 μl/well) of a microplate (ELISA PLATE H TYPE, Sumitomo Bakelite Co., Ltd.) and left at room temperature for 2 hours.
2. The plate is washed 3 times with PBS.
3. PBS containing 1% BSA (Block Ace, Dainippon Pharmaceutical Co., Ltd.) is pipetted into each well (200 μl/well) and left at room temperature for 1 hour for blocking.
4. The plate is washed 3 times with PBS containing 0.05 mass % Tween 20 (SIGMA) (referred to hereinafter as T-PBS).
5. Separately, 0.3 μg/ml rDer f II (Seikagaku Corporation) is diluted $2^n$-fold with 9-tube T-PBS, and each dilution is pipetted as a standard in a volume of 50 μl into each well, while a well to which 50 μl T-PBS is added as a negative control in place of rDer f II is prepared. The sample to be measured is diluted suitably with T-PBS and pipetted in a volume of 50 μl into each well. The plate is left at room temperature for 2 hours.
6. The plate is washed 3 times with T-PBS.
7. HRP-labeled 13A4 (Seikagaku Corporation Co., Ltd) at optimum concentration is pipetted in a volume of 50 μl into each well and left at room temperature for 2 hours.
8. The plate is washed 3 times with T-PBS.
9. A coloration kit T for peroxidase (Sumitomo Bakelite Co., Ltd.) is used in coloration. First, 0.1 ml substrate solution is added to and mixed with 10 mL coloration agent to form a coloration solution. This coloration solution is pipetted in a volume of 100 μl into each well and colored at room temperature. Thereafter, the reaction is terminated by pipetting a termination solution in a volume of 100 μl into each well, and the absorbance at 450 nm is measured with a plate reader.
10. The concentration of Der f II in the sample is calculated by using a calibration curve obtained from the absorbance of each standard.

Using the determined concentrations of Der f II, the degree of removal of allergen by suction with a vacuum-cleaner is defined by the following equation:

$$R = a/(a+b) \times 100 \ (\%)$$

wherein a is the concentration of Der f II in the extract of removed allergen, and b is the concentration of Der f II in the extract of remaining allergen.

The degree of removal of allergen, determined for each sample in the above test, is expressed as Rs. Separately, the same test as the above is conducted except that cleaning with a vacuum-cleaner is conducted without spray treatment, and the degree of removal of allergen in this test is expressed as Rr. The ratio of the degree of removal of allergen with spray treatment to that without spray treatment, that is, Rs/Rr, was divided into 4 ranks under the following criteria and used as an indicator of the effect of removing allergen in each sample.

A: Rs/Rr is 2.0 or more.
B: Rs/Rr is 1.5 to less than 2.0.
C: Rs/Rr is 1.0 to less than 1.5.
D: Rs/Rr is less than 1.0.

(2) Evaluation of Low-Temperature Stability 100 ml samples were introduced into glass bottles PS-No. 11 (Daiichi Glass Kabusikigaisya), and the bottles were capped and stored in thermostatic chambers kept at −5° C. and −10° C. respectively. 30 days after storage, each sample was observed, and whether crystals had been precipitated or not was judged with naked eyes. The judgment results were classified in 3 ranks under the following criteria and used as an indicator of the low-temperature stability of each sample.

⊙: Not crystallized both at −5° C. and −10° C.
○: Crystallized at −10° C. only.
x: Crystallized both at −5° C. and −10° C.

TABLE 1

| | Compounded component | Comparative Example | | | | Example | | | | | |
|---|---|---|---|---|---|---|---|---|---|---|---|
| | (mass-%) | 1 | 2 | 3 | 4 | 1 | 2 | 3 | 4 | 5 | 6 |
| (a) | Ethanol | 15 | 15 | 15 | 15 | 15 | 15 | 15 | 15 | 15 | 15 |
| (b), (b') | Potassium sulfate | | | | 1.2 | 0.41 | 0.78 | 0.78 | 0.78 | 1.17 | 1 |
| | Sodium sulfate | 0.6 | 0.8 | 1.2 | | 0.79 | 0.42 | 0.42 | 0.42 | 0.63 | 0.2 |
| (d) | Methyl dihydrojasmonate | | | | | | | 0.05 | 0.1 | | |
| (e) | Compound A | | | | | | | 0.1 | 0.2 | | |
| (c) | Deionized water | Balance | Balance | Balance | Balance | Balance | Balance | Balance | Balance | Balance | Balance |
| | Total | 100 | 100 | 100 | 100 | 100 | 100 | 100 | 100 | 100 | 100 |

TABLE 1-continued

| Compounded component (mass-%) | Comparative Example | | | | Example | | | | | |
|---|---|---|---|---|---|---|---|---|---|---|
| | 1 | 2 | 3 | 4 | 1 | 2 | 3 | 4 | 5 | 6 |
| Potassium sulfate + Sodium sulfate (mass-%) | 0.6 | 0.8 | 1.2 | 1.2 | 1.2 | 1.2 | 1.2 | 1.2 | 1.8 | 1.2 |
| Potassium sulfate/Sodium sulafte (molar ratio) | 0/1 | 0/1 | 0/1 | 0/1 | 3/7 | 6/4 | 6/4 | 6/4 | 6/4 | 8/2 |
| pH | 7 | 7 | 7 | 7 | 7 | 7 | 7 | 7 | 7 | 7 |
| Effect of removing allergen | B | B | A | A | A | A | A | A | A | A |
| Low-temperarure stability | ◎ | ○ | X | X | ○ | ◎ | ◎ | ◎ | ○ | ○ |

As is evident from Table 1, the low-temperature shelf stability was improved by incorporating the component (b) or (b') in the present invention (combination of potassium sulfate and sodium sulfate), and as a result, the total content could be increased as compared with the case using the single one, and thus the effect of removing allergen was enhanced.

Synthesis Example

Synthesis of Compound A

According to a method described in WO 00/79951, hydroxyethyl cellulose having a weight-average molecular weight of 200,000 wherein the degree of substitution of hydroxyethyl group was 2.5 (manufactured by Hercules), 80% isopropyl alcohol and 48% aq. sodium hydroxide solution were mixed to prepare slurry which was then stirred for 30 minutes in a nitrogen atmosphere at room temperature. A polyoxyalkylene compound represented by the following formula:

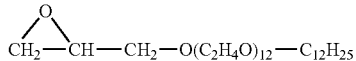

was added thereto, and the mixture was reacted at 80° C. for 8 hours to convert it into polyoxyalkylene. After the reaction was finished, the reaction solution was neutralized with acetic acid, and the reaction product was filtered off. The reaction product was washed twice with isopropyl alcohol and dried for 1 day and 1 night at 60° C. under reduced pressure, and Compound A wherein the degree of substitution of polyoxyalkylene group was 0.014 was obtained.

The invention claimed is:

1. An allergen remover composition comprising the following components (a), (b) and (c):
    Component (a): an organic compound forming an azeotropic mixture with water and having an azeotropic point of lower than 100° C. with water at 1013.25 hpa,
    Component (b): a component which upon evaporation of a liquid component in the allergen remover, forms a solid containing a compound represented by the following formula (1):

$$K_xNa_y(SO_4)_2 \quad (1)$$

wherein x is a number of 0.8 to 3.6, y is a number of 0.4 to 3.2, and x+y is 4,
    Component (c): water
    wherein when component (b) is present, said composition forms a solid containing a compound represented by the following formula (1):

$$K_xNa_y(SO_4)_2 \quad (1)$$

wherein x is a number of 0.8 to 3.6, y is a number of 0.4 to 3.2, and x+y is 4.

2. The composition according to claim 1, wherein the component (a) is at least one member selected from the group consisting of ethanol, 1-propanol and 2-propanol.

3. The composition according to claim 1 or 2, which further comprises an arthropod repellent as component (d).

4. The composition according to claim 1 or 2, which further comprises a water-soluble polymer compound as component (e) which is at least one polymer selected from the group consisting of a cellulose derivative, a processed starch, a (meth)acrylic acid homopolymer, a (meth)acrylic acid copolymer with at least one vinyl monomer, a (meth)acrylic acid copolymer with at least one alkyl ester, a polymer obtained by polymerizing a monomer having a cationic group and a vinyl group or allyl group in the molecule and a salt of said polymers.

5. A method of removing allergen, which comprises cleaning with the allergen remover composition according to claim 1 or 2.

6. The composition according to claim 1, wherein component (a) is at least one selected from the group consisting of ethanol, cyclohexane, cyclohexanol, cyclohexanone, cyclohexane, toluene, 1-butanol, 2-butanol, 1-propanol, 2-propanol, 1-hexanol, hexane, 1-heptanol, 1-pentanol and 2-pentanol.

7. The composition according to claim 1, wherein component (b) is present and x is a number of 1.2 to 3.2.

8. The composition according to claim 1, wherein component (b) is present and x is a number of 1.6 to 2.8.

9. The composition according to claim 1, wherein component (b) is present and y is a number of 0.8 to 2.8.

10. The composition according to claim 1, wherein component (b) is present and y is a number of 1.2 to 2.4.

11. The composition according to claim 1, wherein component (b) is contained such that the total of potassium ion, sodium ion and sulfate ion becomes 0.005 mass % or more.

12. The composition according to claim 1, wherein component (b) is contained such that the total of potassium ion, sodium ion and sulfate ion becomes 0.01 mass % or more.

13. The composition according to claim 1, wherein, component (b) is contained such that the total of potassium ion, sodium ion and sulfate ion becomes 0.1 mass % or more.

14. The composition according to claim 1, wherein the content of component (a) in the allergen remover is 1 to 70 mass %.

15. The composition according to claim 1, wherein component (b) is present in an amount of up to 10 mass %.

16. The composition according to claim 1, wherein component (b) is present in an amount of up to 5 mass % or less.

17. The composition according to claim 1, wherein component (b) is present in an amount of up to 3 mass % or less.

* * * * *